United States Patent [19]

Kellermann et al.

[11] 4,146,436

[45] Mar. 27, 1979

[54] ELECTROCHEMICAL DETERMINATION OF HEAVY METALS IN WATER AND APPARATUS THEREFOR

[75] Inventors: Walter Kellermann; Herbert Nischik; Ferdinand V. Sturm, all of Erlangen, Fed. Rep. of Germany

[73] Assignee: Siemens Aktiengesellschaft, Munich, Fed. Rep. of Germany

[21] Appl. No.: 884,111

[22] Filed: Mar. 7, 1978

[30] Foreign Application Priority Data

Mar. 18, 1977 [DE] Fed. Rep. of Germany ....... 2711989

[51] Int. Cl.$^2$ ............................................ G01N 27/42
[52] U.S. Cl. ................................... 204/1 T; 204/195 R
[58] Field of Search .................. 204/1 T, 1 M, 195 R, 204/195 H

[56] References Cited

U.S. PATENT DOCUMENTS

| | | | |
|---|---|---|---|
| 3,904,487 | 9/1975 | Lieberman et al. | 204/1 T |
| 4,058,446 | 11/1977 | Zirino et al. | 204/195 R |

OTHER PUBLICATIONS

M. Christian Zbinden, Bull. Soc. Chim. Biol., 13, 35 (1931).

Samuel S. Lord, Jr. et al., Analytical Chem., vol. 24, No. 1, pp. 209–213 (1952).

M. G. Tamba et al., J. Electoanal. Chem., 25, No. 2, pp. 235–244 (1970).

C. O. Huber et al., Analytical Chem, vol. 38, No. 1, pp. 128–129 (1966).

*Primary Examiner*—G. L. Kaplan
*Attorney, Agent, or Firm*—Kenyon & Kenyon, Reilly, Carr & Chapin

[57] ABSTRACT

A method for electrochemically determining the concentration of heavy metals in water by precipitating the metals at a solid electrode under the influence of a constant negative d-c voltage and subsequently dissolving them by anodic oxidation, in which the metals are precipitated at a platinum metal electrode; the water is then replaced by an electrolytic solution and the precipitated metals are dissolved again by suddenly changing the negative d-c voltage into a constant positive d-c voltage, while the electric charge required for the dissolution is determined and the concentration is determined therefrom; the time of application and the magnitude of the d-c voltage are always kept constant during the precipitation as well as during the dissolution of the metals.

14 Claims, 3 Drawing Figures

ELECTROCHEMICAL DETERMINATION OF HEAVY METALS IN WATER AND APPARATUS THEREFOR

BACKGROUND OF THE INVENTION

This invention relates to a method for electrochemically determining the concentration of heavy metals in water by precipitation of the metals at a solid electrode under the influence of a constant negative d-c voltage, where the water containing the metals is brought into contact with the solid electrode for a specific length of time under constant flow conditions, and by subsequent dissolution of the metals by anodic oxidation, the precipitation process and the dissolution process being repeated continuously. This invention further relates to apparatus for implementing this method.

In the context of environmental protection, the monitoring of industrial waste water, particularly with respect to the content of heavy metal ions, prior to entering a biological purification facility, is of great importance, since poisoning of the live sludge by heavy metal ions, i.e., an inhibition of the biochemical breakdown process, can lead to a lengthy shutdown of the purification plant. Due to their toxicity, heavy metal ions such as those of copper, zinc, cadmium and lead, can furthermore cause damage to the living organisms present in the waters.

The heavy metal content can be determined by various electrochemical methods. At low concentrations, the polarographic methods are particularly well suited for this purpose (see: R. Neeb, "Inverse Polarography and Voltammetry", Verlag Chemie GmbH, Weinheim/Bergstr., 1969, pages 1 to 5). In polarography, the metal ions are reduced and precipitated at a negative working electrode in apparatus including a working electrode, particularly a mercury dropping electrode, a counterelectrode and a reference electrode. The potential of the working electrode is varied at a defined rate and the diffusion limit current is used for the metal determination. In the so-called inverse polarography, an enrichment electrolysis is performed prior to the determination itself, where the metal ions to be determined are precipitated at electrodes of constant surface area at potentials which are more negative than the half-step potentials. The quantity of the precipitated metal depends primarily on the concentration and the duration of the electrolysis as well as, possibly, on the stirring conditions. If, subsequent to the precipitation, the potential of the working electrode is varied at a defined constant rate to anodic values, the metal is anodically oxidized and dissolved again partially at a definite potential. In the current waveform, this manifests itself in a peak which is evaluated.

These polarographic methods, while exhibiting high accuracy and sensitivity, require expensive equipment and have a number of inherent disadvantages. For, an electrolytic liquid of defined composition, i.e., of definite conductivity and a definite $p_H$ value, is required for the determination, and additives must therefore be admixed to the water to be analyzed such as conductive salts and complex formers. In addition, care must also be taken that the temperature is constant. It is further necessary to generate a defined stationary mercury drop before every determination. Since the generation of such drops cannot be automated, polarographic methods are hardly suitable for automatic operation, which is advisable, for instance, for monitoring waste waters and water bodies. Finaly, mercury is also consumed in these methods and the electrodes have only a short life.

In a voltametric method known from U.S. Pat. No. 3,904,487 for determining trace metals, mercury electrodes are likewise used, and specifically in the form of solid electrodes, in which a mercury film is provided on the inside surface of an electrode body of graphite. In this method, the metals, i.e., zinc, cadmium, lead and copper, are precipitated under the influence of a constant negative d-c voltage, i.e., at a potential of $-1.4$ V (as measured against an Ag/AgCl electrode as the reference electrode). Then, the potential is increased steadily to $+0.5$ V, whereby the metals are dissolved again at discrete values. During the metal precipitation and dissolution, the metal containing sample solution flows past the two electrodes with a constant flow velocity. The precipitation and dissolving process can be repeated, but the sample solution must be renewed each time. One disadvantage of this method is that unattended operation is not possible, since the electrode surface, i.e., the mercury film, must be recreated prior to every measurement. Furthermore, the detection of and analysis for mercury are not possible, and in addition, mercury containing water accumulates as a waste product with this method, since the mercury film is likewise oxidized after the metal determination proper and is thereby removed from the electrode body.

SUMMARY OF THE INVENTION

It is the object of the present invention to develop a method for electrochemically determining the concentration of heavy metals in water through precipitation of the metals at a solid electrode under the influence of a constant negative d-c voltage and subsequent dissolution of the metals by anodic oxidation, in such a manner that it can be used for the automatic and unattended determination, recording and monitoring of the heavy metals in water. At the same time, difficulties which result from the use of mercury electrodes are to be avoided.

According to the present invention, this is achieved by: precipitating the metals at a metal electrode of the platinum family; after the precipitation of the metals, replacing the water by an electrolyte solution, dissolving the precipitated metals again by a sudden change of the negative d-c voltage into a constant positive d-c voltage, during which the electric charge required for the dissolution is determined and the concentration determined therefrom; and maintaining the application time and the magnitude of the d-c voltage always constant during the precipitation as well as during the dissolution of the metals.

Platinum family metals are understood to be the metals ruthenium, rhodium, palladium, osmium, iridium and platinum, i.e., the elements with the atomic numbers 44 to 46 and 76 to 78 of the periodic system of the elements.

It is particularly advantageous in the method according to the present invention that pretreatment of the water to be analyzed can be dispensed with, i.e., no additives need to be admixed to the water in order to set a given conductivity and a given $p_H$ value. There is furthermore no removal of oxidizable or reducible organic substances. As compared to polarographic methods, an electrolytic liquid of defined composition is used in the method according to the invention only in dissolving the metals; the precipitation, on the other hand, is carried out directly in the water to be analyzed. The advantage, which is obtained by omitting the pretreatment of the water, consists in particular of time and effort savings. Thus, the operating personnel of a purification plant have available within a very short time the report on the presence of heavy metals in the water, so that appropriate countermeasures can be initiated without loss of time.

By using an electrolytic liquid during the dissolution process, the interfering influences which can occur particularly in the presence of oxidizable organic substances which are present in communal waste waters are eliminated in the method according to the invention. For, if such materials are present, too high a charge value would be obtained and, in addition, the charge value would also not be constant, as the portion based on the oxidation of organic substances depends on the content of these substances in the waste water. The purpose of this step is, thus, not so much to make available a solution with a definite electrolyte content and, thereby, sufficient conductivity, but rather to eliminate the disturbuting influence of impurities contained in the waste water.

Besides the advantages mentioned above, the method according to the present invention is also distinguished by the fact that it does not require the maintenance of a constant temperature. It is therefore suitable for unattended, automatically operating measuring stations.

In the method according to the present invention it is important that the water containing the metals be brought into contact with the solid electrode during the precipitation under constant flow conditions. Constant flow conditions are understood here to be the conditions that the flow velocity of the liquid is constant and the geometrical arrangement of the working electrode in the measuring cell remains the same. An additional possibility for adjusting reproducible flow conditions at the working electrode is to move the electrode itself, using, for instance, electrodes which vibrate with constant frequency or rotate with constant speed. In the method according to the present invention, the constant flow conditions are important for the reason that, by bringing the metal ions from the solution to the electrode on the basis of the concentration gradient alone, i.e., without flow, reproducible precipitation conditions and, thus, reproducible measurement values would not be obtained. For, any accidental shock of the measuring cell as well as temperature and density differences would lead to uncontrollable convection, which would interfere with the development of a constant diffusion layer thickness. However, only through imposition of a reproducibly adjustable flow boundary layer can the diffusion layer be made reproducible. In order to obtain maximum sensitivity, the diffusion layer should moreover be as small as possible. This can advantageously be achieved by arranging for a strong flow against the active surface of the working electrode.

The flow conditions required for the method according to the present invention can be achieved in various ways. Thus, particularly if samples are taken continuously, the water can flow past the working electrode continuously, whereby the measurement value is obtained by averaging over the entire reduction time. The water can be conducted past the electrode, once, but it can also be circulated in a closed loop, for instance, by means of a pump. Preferably, however, the constant flow conditions are set in such a manner that the liquid contained in a measuring cell, i.e., the water to be analyzed, is stirred vigorously. This method is of interest particularly if the mode of operation is discontinuous. The two methods mentioned above can, finally, also be combined, which is advisable particularly for small measuring cells.

Apparatus for implementing the method according to the present invention consists preferably of a measuring cell which is provided with a feed and discharge line for the water to be examined and for the electrolyte solution and which contains a working electrode and a counterelectrode, and of means for providing a precipitation voltage and a dissolution voltage as well as for determining the electric charge required for dissolving the metal.

Such a device is accordingly distinguished by simple design, as only two electrodes are required in the measuring cell and the electrodes operate for an extended period of time without the need for adjustment. The elimination of a reference electrode provides the further advantage that disturbances which could be caused by an effect of the water sample on the reference electrode are thereby eliminated. Because only two electrode are used, the method according to the present invention does not operate potentiostatically but with constant voltage.

As compared with the polarographic methods, the anodic oxidation does not take place steadily in the method according to the present invention, but due to a sudden change of the voltage, where the constant negative d-c voltage prevailing during the precipitation is replaced by a constant positive d-c voltage. In addition, it is not the height of a peak in the current waveform which is evaluated in the method according to the present invention, but the electric charge which must be supplied for dissolving the metals. This quantity is advantageously determined by means of an integrator, and is then recorded. The determination of the concentration is then accomplished by comparison with calibration curves.

Contrary to the Hg electrodes of the known methods, the metals are completely oxidized at the solid electrode in the method according to the present invention. In this manner, no additional error occurs, as is the case due to the dissolution of different partial quantities if liquid electrodes are used. The continuous flow against the working electrode in the method according to the present invention provides the additional advantage that, even for longer measuring point sequences, averaging of the metal contents over the time of the cathodic precipitation can be obtained. If the sample is taken discontinuously, as is the case with the known methods, however, only an instantaneous value can be secured.

Compared to the method known from U.S. Pat. No. 3,904,487, the method according to the present invention has the further advantage that it also allows detecting mercury, which is important particularly for monitoring the environment, and that no mercury accumulates that pollutes the environment. The method according to the present invention, in addition, requires no reference electrodes which, as experience shows, require maintenance, and it therefore operates free of maintenance. With this method, furthermore, the total metal content is determined, which results in very simple evaluation, also by automatic equipment. In contrast thereto, the evaluation of individual peaks, as is the case with the known method, is very complicated and time consuming. With that method, a further disadvantage is that the sample solution and the mercury plating solution must be treated with nitrogen to remove the oxygen, which, as is known, takes considerable time. In addition, it would seem that the known method is usable only for the analysis of salt or sea water which is relatively clean, while the method according to the present invention is suitable particularly for waste waters which in general carry heavy impurities.

While the use of platinum electrodes for voltametrical purposes is known per se (cf., R. Neeb, loc.cit., page 102), considerable difficulties have been encountered heretofore regarding reproducibility. To ensure reproducibility, it is necessary to bring the electrode surface to a defined state by an elaborate pre-treatment prior to every measurement. Such a pre-treatment includes, for instance the following steps in the case of platinum electrodes:

anodic oxidation in perchloric acid $HClO_4$ at 500 uA treatment with freshly prepared aqua regia and subsequent careful rinsing with water cathodic reduction at 500 uA in perchloric acid deaerated with nitrogen storage at 0 V (as measured against a saturated calomel electrode) in perchloric acid deaerated with nitrogen.

Such an expensive pre-treatment of the platinum or platinum family metal electrodes is not necessary with the method according to the present invention. For, in this method, the reproducibility is achieved by the fact that the application time and the magnitude of the d-c voltage always remain constant during the reduction as well as also during the oxidation of the metals. With this regular voltage rhythm, which can be produced in a simple manner by a control unit, each precipitation phase together with the following dissolution phase therefore represents a defined pretreatment of the working electrode for the succeeding measurement. It is important in this connection that a uniform, uninterrupted voltage rhythm is adhered to. It has further been found advantageous to subject the working electrode to this voltage rhythm for some time upon starting up, i.e., prior to the measuring process proper.

In the method according to the present invention, the precipitation of the metals takes place preferably at a voltage in the range between about $-1$ and $-4$ V, especially in the range between about $-1.5$ and $-2.5$ V. The dissolution takes place preferably at a voltage in the range between about $+0.5$ and $+3$ V, especially between about $+0.8$ and $+2$ V. Higher voltages should generally be avoided, since, otherwise, the increasingly appearing electrolysis of the water could become noticeable as interference. Within the scope of the present invention, constant voltage is understood to be a voltage which can deviate up to $\pm 2\%$ from the predetermined value.

The precipitation of the metals takes place in general between 10 seconds and 1 hour, depending on the concentration of the metals to be detected. The metals are preferably precipitated in a time of between about 1 and 10 minutes. As an example, a precipitation period of 5 min. at a voltage of $-2$ V is mentioned. The dissolution of the metals takes place preferably in a time between about 1 second and 1 minute. The dissolving can take, for instance, 60 seconds at a voltage of $+1$ V or 45 seconds at $+2$ V.

By means of the method according to the present invention, the total amount of heavy metal ions present in waters is determined. Although it is also possible, by proper choice of suitable precipitation and dissolution voltages, to determine the metals selectively or by groups, global determination is generally sufficient in practice. Particularly in waste water technology, if, for instance, the biological settling stage is to be protected from poisoning by heavy metal ions, the sum determination furnishes the most important criterion for a possible disturbance.

Heavy metals are generally understood to be metals, the specific gravity of which is above 5. By means of the method according to the present invention, especially the heavy metals which occur frequently in waste waters, such as nickel, copper, zinc, cadmium, tin, mercury and lead are determined.

In the method according to the present invention, a platinum metal electrode can likewise be used to particular advantage as the counterelectrode and, then, the functions of working electrode and counterelectrode can be interchanged after each measurement operation. By this measure the counterelectrode is cleaned during each precipitation phase by oxidation and is particularly well prepared in this manner for use as the working electrode during the succeeding measurement. Such an alternating operation of working and counterelectrode provides various advantages, as it is possible to prevent the activity of the working electrode from decreasing with time, which can be the case particularly through the influence of mercury and other inhibitors and which is due to the fact that the precipitation phase generally takes longer than the dissolution phase. The harmful effect of metals and inhibitors in the form of organic substances, which are deposited as colloids on the electrode surface, could be also eliminated, it is true, by longer oxidation times or by separate cleaning operations, particularly of a mechanical nature, between two measurements; but such measures would lead to a lengthening of the measurement process, which is not desirable. It is therefore advantageous, according to the present invention, to interchange the functions of the working and the counterelectrode after each cycle, as here, besides the gain of time, a very intensive oxidizing cleaning of the counterelectrode takes place, whereby harmful substances, such as inhibitors, can be removed from the electrode surface. In addition, a further positive effect is that a very exact mercury determination is also possible and that the measurement results for the other heavy metals to be determined, such as copper, are not influenced by the presence of mercury ions.

The alternating operation proceeds, for example, as follows: After starting, the measuring cell is filled with the sample solution within 10 seconds; then, the precipitation of the heavy metals takes place within 5 minutes at electrode I, which is at first the working electrode. During this time, electrode II, which is initially the counterelectrode, is cleaned. In the course of the succeeding measuring process itself at electrode I, i.e., during the dissolving of the metal using an electrolyte solution while during about 45 seconds a positive d-c voltage is applied to the working electrode and a negative d-c voltage to the counterelectrode, metal precipitation can already take place at electrode II. In order to preclude any falsification of the measuring result of the subsequent measurement by such precipitation, a brief post-cleaning period is interposed prior to the precipitation phase proper at electrode II by applying to this electrode, following the dissolution process at electrode I, for a short time, i.e., for about 20 sec, a positive d-c voltage (about $+1$ V) in the presence of the electrolyte solution. Replacing the electrolyte solution with a fresh sample solution, a new precipitation-dissolution cycle now follows, in which electrode II becomes the working electrode, while electrode I serves as the counterelectrode and an oxidizing cleaning process takes place there in the course of the precipitation of the metals at electrode II. After the succeeding measuring operation at the electrode II and the post-cleaning of electrode I, the latter then becomes the working electrode again in another cycle. With such an alternating mode of operation it is necessary that electrodes I and II be of identical design, i.e., consist of the same material such as platinum and have the same surface and geometry, and that also the same flow conditions prevail at both electrodes. The switching of the electrodes in alternating operation can be performed by a control unit which also supplies the other command signals required with the method according to the present invention.

DETAILED DESCRIPTION OF THE INVENTION

Figure 1:
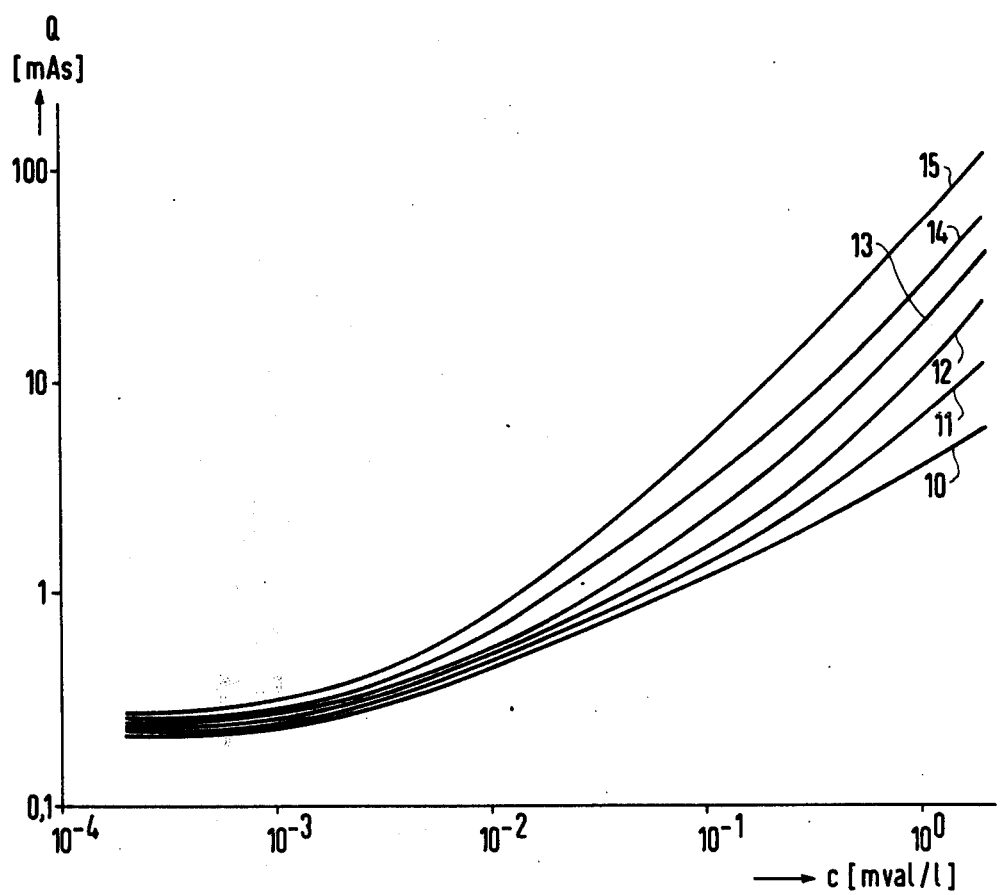
FIG. 1 shows a series of calibration curves for carrying out the method of the present invention.

To provide calibration curves, "synthetic waste water" was prepared, in which definite amounts of heavy metal salts were added to tap water. In FIG. 1, a number of calibration curves is shown. The curves were obtained using copper salt solutions of different concentrations and with different precipitation times. The copper concentration was between $10^{-3}$ and $10^{-7}$ mol $Cu^{2+}$/l, i.e., 2 to $2 \times 10^{-4}$ mval $Cu^{2+}$/l. The conductivity of such copper salt solutions is between 1.3 and 1.6 mS/cm (millimho/cm). The reduction was carried out at a voltage of $-1.5$ V and the oxidation at $+0.8$ V. For the oxidation, a 0.1 molar $Na_2So_4$ solution with a pH value adjusted to 3.5 was used as the electrolytic liquid. As the working electrode, Pt electrode with a surface of 20 mm$^2$ was used. In FIG. 1, the charge Q in mAsec is plotted along the ordinate and the concentration c of $Cu^{2+}$ in mval/l along the abscissa; the curves 10 to 15 apply to reduction times of 0.5, 1, 2, 3, 5 and 10 minutes.

In the examination of an industrial waste water, polarographic analysis showed a content of $5 \times 10^{-6}$ mol $Cu^{2+}$ ($10^{-2}$ mval) and $3.5 \times 10^{-6}$ mol $Ni^{2+}$ ($7 \times 10^{-3}$ mval) per liter as well as a zinc content of less than $10^{-7}$ mol (less than $2 \times 10^{-4}$ mval) per liter. A determination was preformed in accordance with the method of the present invention with a precipitation voltage of $-1.5$ V (duration, 3 min.) and a dissolution voltage of $+0.8$ V. For the metal dissolution, an electrolyte liquid consisting of a 0.1 molar $Na_2So_4$ solution with a pH value of 3.5 was used. The investigation showed an electric charge to be supplied for dissolving the metal of about 0.7 mAsec. Through comparison with Curve 13 as per FIG. 1 one obtains therefrom a heavy metal ion content of $1.4 \times 10^{-2}$ mval/l. The deviation from the polarographic method is therefore about $-18\%$. After adding $10^{-2}$ mval $Cu^{2+}$/l to the waste water, a measured heavy metal ion content of $2.5 \times 10^{-2}$ mval/l was obtained with the method according to the present invention and a deviation from the polarographically determined value of $-8\%$. Analyses on copper, cadmium and lead containing waters showed results.

In checking a communal waste water, heavy metal ions could not be detected by the method according to the present invention nor polarographically, i.e., the heavy metal ion concentration was below the detection limit of $10^{-3}$ and $10^{-4}$ mval/l, respectively. Upon adding $1 \times 10^{-2}$ mval $Cu^{2+}$/l to this waste water, it was possible to determine the added amount of copper nearly quantitatively by means of the method according to the invention; the deviation was only 5%.

These investigations show that the method according to the invention is suitable particularly for indicating that a critical heavy metal ion concentration in waters is exceeded, and therefore provides the possibility of monitoring in a simple, maintenance free, nearly continuous and automatic manner.

Figure 2:
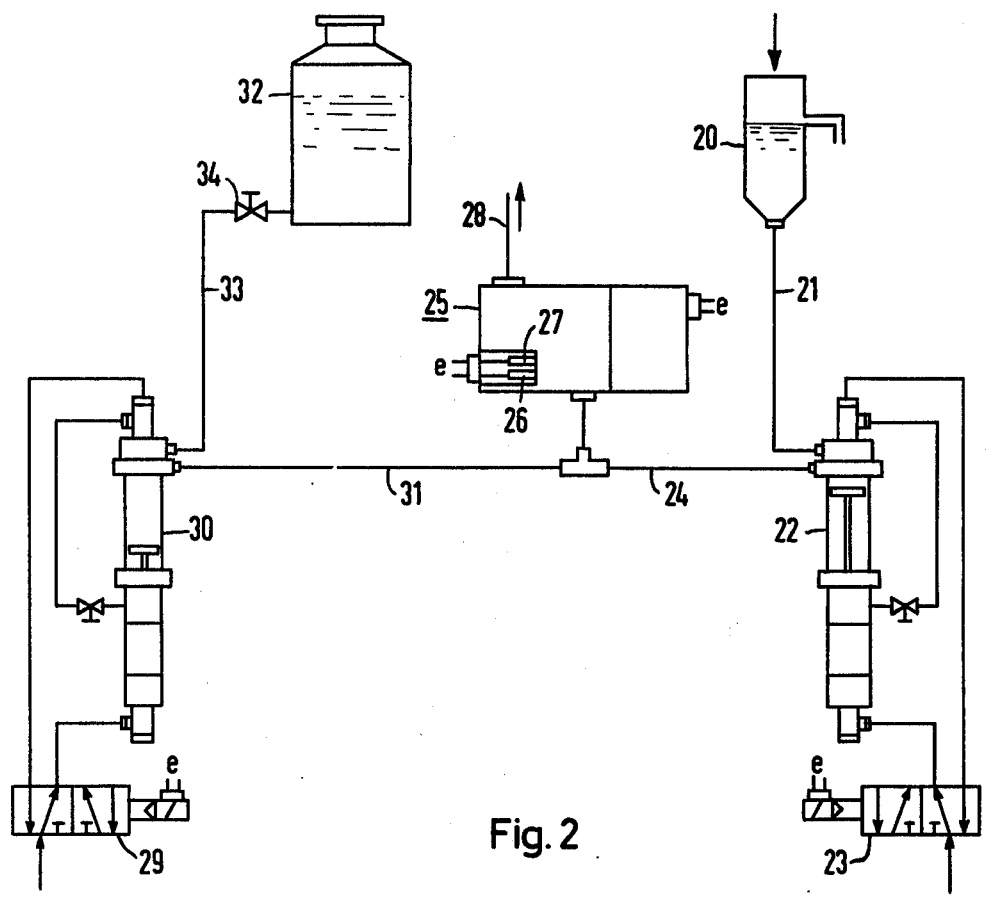
FIG. 2 is a schematic diagram illustrating apparatus for carrying out an electrochemical determination of heavy metals in water in accordance with the present invention.

In FIG. 2, a device for implementing the method according to the present invention is shown schematically. The water to be analyzed is first pumped into a filter, not shown in FIG. 2, in which mechanical impurities are held back. From the filter, the water reaches an overflow vessel 20 and flows from there through a line 21 into a pneumatically operated cylinder burette 22. The latter receives its operating signals from an electrically operated slide valve 23. The water (quantity, 5 ml) is pushed from the cylinder burette 22 into a measuring cell 25 through a line 24 by means of compressed air (pressure, 3 to 8 bar).

The measuring cell 25 has two electrodes 26 and 27, a working electrode and a counterclockwise, in the form of platinum wires (diameter, 1 mm), which together with their leads are cast into epoxy resin and the plane active surfaces of which are ground and polished. The liquid in the measuring cell can be moved by means of a magnetic stirrer. To establish the necessary constant flow conditions, one can, however, also proceed in such a manner that the electrode pair is introduced into a pump, with very little spacing from the rotor or the rotor vanes, for instance, with a spacing of about 0.3 mm. If the pump has, for instance, a three-vane rotor, 140 rotor vanes move past the active surfaces of the two electrodes per second at a speed of 2800 RPM, i.e., the flow against the electrodes is extremely vigorous. Preferably, a pump is used in this connection, in which an electric motor drives the rotor via a magnetic coupler, as then no problems with the sealed shaft feedthrough arise and the device can therefore be operated without maintenance over an extended period of time. The ring magnet should further be cast-in hermetically, so that the water and the electrolytic liquid do not come into contact with metal parts; the pump housing itself consists of plastic such as Plexiglas, and the rotor vanes are of hard rubber. Such a measuring cell consists, for instance, of a cylindrical pump body (diameter, 60 mm × 45 mm), onto which the pump head (diameter 60 mm × 22 mm) is bolted. The two electrodes are screwed into the pump head.

After the metal precipitation is completed, the water is removed from the measuring cell 25 via a line 28. This is accomplished by bringing electrolyte liquid (quantity, 5 ml) into the measuring cell by means of a cylinder burette 30, operated via a slide valve 29, through a line 31, for instance, a $10^{-3}$ molar NaCl solution with a pH value of 3.5. The electrolyte liquid gets from a supply tank 32 via a line 33 into the cylinder burette 30; a shutoff valve 34 is arranged in the line 33. After the metal is dissolved, the electrolyte liquid is removed again from the measuring cell in a similar manner by aqueous sample solution.

5-way valves with two functions are used as the slide valves 23 and 29. Electronic circuits, not shown in FIG. 2, insure that the cylinder burettes 22 and 30 as well as the stirrer motor are operated at the right time and that the then required voltages are applied to the two electrodes. The connections for the electronic circuits at the motor, the electrodes and the slide valves are designated in FIG. 2 with e.

The oxidation, i.e., the dissolution of the metals, is generally performed, as is the metal precipitation, with the liquid in flowing condition. Liquid flow is not absolutely required, however, so that the metals can be dissolved even if the electrolyte does not move. In general an aqueous NaCl or $Na_2SO_4$ solution can be used as the electrolyte liquid, preferably with a content between about $10^{-1}$ and $10^{-3}$ mol/l. The pH value of the electrolyte liquid is between 1 and 7; preferably it is between about 3 and 4.

Approximately 5 ml of electrolyte liquid are required for one measurement in the method according to the present invention. This means that, with a duration of a measuring cycle of between 6 and 7 minutes, only about 30 to 35 l of electrolyte liquid are consumed in the course of a month with uninterrupted operation. With an appropriate electrolyte supply, a very long maintenance free operating time is thus obtained. The duration of about 6 to 7 minutes is based on a reduction time of 5 min., with which in general sufficient sensitivity is obtained. If increased sensitivity is required, the reduction time must be lengthened. If, on the other hand, the measuring point sequence is to be minimized, then the reduction time must be chose shorter, at the expense of the sensitivity.

The active surface of the electrodes, particularly that of the working electrode, is advantageously made flat. In the case of the working electrode, the area of this active surface is preferably about 0.8 mm$^2$, i.e., a platinum metal wire with a diameter of about 1 mm is used, in which only one of the end faces is exposed. However, the active electrode area can also be as large as 20 mm$^2$ and more. For alternating operation, the counterelectrode must have the same active surface area as the working electrode. If during operation, the functions of working electrode and counterelectrode are not interchanged, then the active area of the counterelectrode is advantageously larger than that of the working electrode, since then the potential of the counterelectrode can largely be kept constant.

Besides platinum, palladium can also be used to particular advantage as the electrode material. The shape of the electrode need not be in the form of a pin or a wire, where the active surface is flat; the electrodes can also consist of coiled wire or only the counterelectrode can consist of coiled wire which then surrounds, for instance a pinshaped working electrode. To reduce the flow resistance, the two electrodes can also be designed as cylinders and be embedded one behind the other in a ceramic, glass or plastic tube. The electrodes can also be arranged as concentric cylinders in a flow tube, the outer cylinder representing, with its larger surface area, the counterelectrode. Finally, a ring shaped or cylindrical shaped counterelectrode can also surround a pin shaped working electrode. The working electrode, furthermore, can rotate or vibrate, as then, as is the case with stirring the water sample, an improved diffusion transport of the metal ions takes place.

Figure 3:
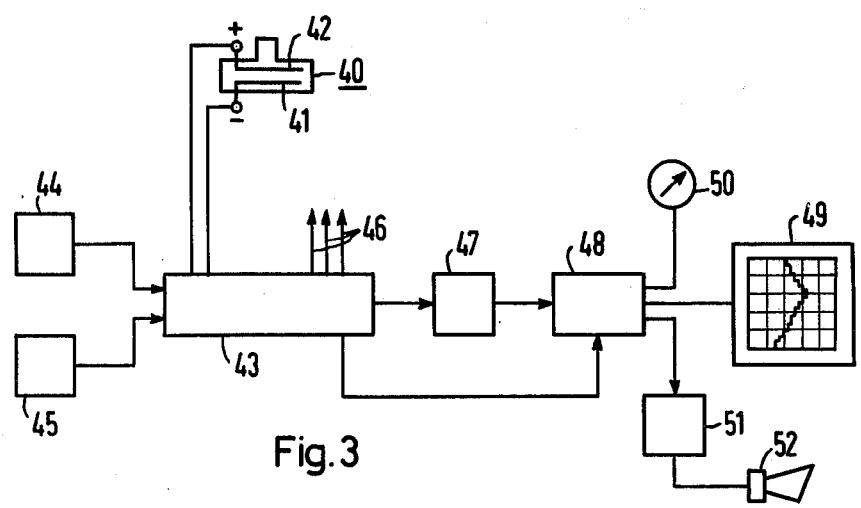
FIG. 3 is a block diagram of the electrical control system for use with an embodiment such as that of FIG. 2.

In FIG. 3, a preferred embodiment of a complete arrangement for determining the heavy metal ion concentration according to the method of the present invention, a so-called heavy metal ion detector, is shown. A measuring cell 40 with a working electrode 41 and a counterelectrode 42 is connected to a control unit 43. The liquid contained in the measuring cell can be stirred, for instance, by means of a magnetic stirrer, not shown in FIG. 3. By means of voltage sources 44 and 45, the precipitation and the dissolution voltage for the working electrode 41 is provided via the control unit 43. From the control unit 43, as indicated by arrows 46, slide or magnetic valves, not shown in FIG. 3, for feeding in and discharging the sample solution, i.e., the water, and the electrolyte solution, to and from the measuring cell are also actuated. The current flowing during the oxidation of the metals precipitated at the working electrode 41 is integrated over the time in an integrator 47. After a predetermined time, for instance, after every 5 seconds, after which the metals are already almost completely dissolved, the signal from the integrator 47 is briefly interrogated and the value of the charge determined is stored in an analog storage device 48 i.e., a sample and hold circuit, and converted into a voltage proportional to the measurement value. The voltage values are then recorded on a line recorder 49 or a dot printer calibrated in mval/l. An indicating instrument 50, calibrated in mval/l, can also be connected. In addition, a limit contact 51 may be provided, which is closed if a predetermined value is exceeded, and triggers an alarm device 52.

What is claimed is:

1. In a method for electrochemically determining the concentration of heavy metals in water by precipitation of the metals at a solid electrode under the influence of a constant negative d-c voltage between the solid electrode and a counter electrode, comprising bringing the water containing the metals into contact with the solid electrode for a time under constant flow conditions, and subsequently dissolving the metals by anodic oxidation, the precipitation and dissolution steps being repeated continuously, the improvement comprising precipitating the metals at a platinum family metal electrode; using a platinum family electrode as the counterelectrode; after the metals are precipitated replacing the water with an electrolyte solution; dissolving the precipitated metals again by suddenly changing the negative d-c voltage into a constant positive d-c voltage, determining the electric charge supplied for the dissolution and from said charge the concentration; interchanging the functions of the working electrode and the counterelectrode each time said charge is determined; and always maintaining the application time and the magnitude of the d-c voltage constant during the precipitation as well as during the dissolution of the metals.

2. The method according to claim 1, wherein the precipitation of the metals is performed at a voltage in the range between about −1 and −4 V.

3. The method according to claim 2 wherein said voltage is in the range between about −1.5 and −2.5V.

4. The method according to claim 1, wherein the metals are precipitated in a time period of between about 1 and 10 minutes.

5. The method according to claim 1 wherein the dissolution of the metals is performed at a voltage in the range between about +0.5 and +3 V.

6. The method according to claim 5 wherein said voltage range is between about +0.8 and +2 V.

7. The method according to claim 1, wherein the metals are dissolved in a time period of between about 1 second and 1 minute.

8. The method according to claim 1, wherein the electrolyte is selected from an aqueous sodium chloride and a sodium sulfate solution.

9. The method according to claim 8 wherein said solution has a content of between $10^{-1}$ and $10^{-3}$ mol/l.

10. The method according to claim 1, wherein said electrolyte solution has a pH value of between about 3 and 4.

11. Apparatus for determining the concentration of heavy metals in water comprising:
    (a) a measuring cell having a working electrode and a counterelectrode, said working electrode and said counterelectrode both made from a metal of the platinum family;
    (b) inlet and outlet lines to said measuring cell;
    (c) means to establish constant flow conditions in said cell;
    (d) means to alternately supply water and an electrolyte solution to said cell through said inlet line and at the same time alternately discharging, through said outlet line, electrolyte solution when water is being supplied and water when electrolyte solution is being supplied;
    (e) means for providing a constant negative d-c precipitation voltage to said working electrode for a first fixed time while said water is in said cell to precipitate the metals in said water on said working electrode;
    (f) means for suddenly changing said negative voltage to a constant positive voltage when said electrolyte is in said cell to dissolve said precipitated metals for a second fixed time;
    (g) means for measuring the electric charge required for dissolving said precipitated metals; and
    (h) means for interchanging the functions of the working electrode and the counterelectrode after every measuring operation.

12. Apparatus according to claim 11, wherein said electrodes consist of platinum.

13. Apparatus according to claim 11, wherein the counterelectrode has the same active area as the working electrode.

14. Apparatus according to claim 11, wherein the active surface of the electrodes is flat.

* * * * *